(12) United States Patent
Manna et al.

(10) Patent No.: US 11,584,915 B2
(45) Date of Patent: Feb. 21, 2023

(54) COMPOSITIONS AND METHODS FOR REMEDIATION OF SULFATE REDUCING PROKARYOTES

(71) Applicant: MC (US) 3 LLC, Wilmington, DE (US)

(72) Inventors: Kathleen Manna, Collegeville, PA (US); Ian A. Tomlinson, Midland, MI (US); Abhiram Thatipelli, College Station, TX (US); Christopher Janes, College Station, TX (US); Elizabeth J. Summer, College Station, TX (US)

(73) Assignee: MC (US) 3 LLC, Wilmington, DE (US)

(*) Notice: Subject to any disclaimer, the term of this patent is extended or adjusted under 35 U.S.C. 154(b) by 0 days.

(21) Appl. No.: 16/630,201

(22) PCT Filed: Jul. 6, 2018

(86) PCT No.: PCT/US2018/041066
§ 371 (c)(1),
(2) Date: Jan. 10, 2020

(87) PCT Pub. No.: WO2019/014061
PCT Pub. Date: Jan. 17, 2019

(65) Prior Publication Data
US 2020/0154715 A1    May 21, 2020

Related U.S. Application Data

(60) Provisional application No. 62/531,568, filed on Jul. 12, 2017.

(51) Int. Cl.
| | |
|---|---|
| *C12N 1/20* | (2006.01) |
| *A01N 63/27* | (2020.01) |
| *C02F 1/50* | (2006.01) |
| *C02F 3/34* | (2006.01) |
| *C07K 14/21* | (2006.01) |
| *C09K 8/582* | (2006.01) |
| *A01N 63/50* | (2020.01) |
| *C02F 103/10* | (2006.01) |
| *C12R 1/385* | (2006.01) |

(52) U.S. Cl.
CPC ............ *C12N 1/205* (2021.05); *A01N 63/27* (2020.01); *A01N 63/50* (2020.01); *C02F 1/50* (2013.01); *C02F 3/34* (2013.01); *C07K 14/21* (2013.01); *C09K 8/582* (2013.01); *C02F 2103/10* (2013.01); *C02F 2303/04* (2013.01); *C12R 2001/385* (2021.05)

(58) Field of Classification Search
None
See application file for complete search history.

(56) References Cited

U.S. PATENT DOCUMENTS

| | | | |
|---|---|---|---|
| 6,551,795 B1 | 4/2003 | Rubenfield et al. | |
| 7,052,901 B2 * | 5/2006 | Crews | C09K 8/605 435/281 |
| 2008/0113406 A1 | 5/2008 | Martin et al. | |
| 2008/0286236 A1 | 11/2008 | Gebhart et al. | |
| 2012/0214713 A1 * | 8/2012 | Mu | C12N 1/36 507/201 |
| 2012/0277126 A1 * | 11/2012 | Fallon | C09K 8/582 507/201 |
| 2014/0315765 A1 * | 10/2014 | McDaniel | C09K 8/68 507/201 |
| 2015/0259642 A1 * | 9/2015 | Sangwai | C09K 8/52 435/253.3 |
| 2015/0352610 A1 * | 12/2015 | Carpenter | B09C 1/10 405/128.75 |

FOREIGN PATENT DOCUMENTS

| | | |
|---|---|---|
| WO | WO 2012/064660 | 5/2012 |
| WO | WO 2016/081239 | 5/2016 |
| WO | WO 2019/014061 | 1/2019 |

OTHER PUBLICATIONS

Nakayama, K. et al. "The R-Type pyocin of Pseudomonas aeruginosa is related to P2 phage, and the F-type is related to lambda phage" Molecular Microbiology, vol. 38, No. 2. Oct. 1, 2000. pp. 213-231.
International Search Report and Written Opinion, dated Oct. 9, 2018 in corresponding International Patent Application PCT/US2018/041066, filed Jul. 6, 2018.
Communication Under Rules 161(1) and 162 EPC issued in corresponding European Patent Application No. 18746411, dated Feb. 19, 2020.
Response to Communication filed in European Patent Application No. 18746411, filed Aug. 26, 2020.

* cited by examiner

*Primary Examiner* — John J Figueroa
(74) *Attorney, Agent, or Firm* — Howson & Howson, LLP; Colleen M. Schaller

(57) ABSTRACT

Compositions and methods are provided for use in controlling souring and corrosion causing prokaryotes, such as SRP, by treating oil and gas field environments or treatment fluids with a newly identified bacterial strain ATCC Accession No. PTA-124262 as a self-propagating whole cell that produces an anti-SRP bacteriocin in situ. In another aspect, the methods use one or more toxic peptides or proteins isolated therefrom in methods to control unwanted prokaryotic growth in these environments.

5 Claims, No Drawings
Specification includes a Sequence Listing.

SEQUENCE LISTING

<160> NUMBER OF SEQ ID NOS: 4

<210> SEQ ID NO 1
<211> LENGTH: 177
<212> TYPE: PRT
<213> ORGANISM: Pseudomonas aeruginosa

<400> SEQUENCE: 1

Met Ser Ser Arg Leu Leu Pro Pro Asn Arg Ser Ser Leu Glu Arg Ser
1               5                   10                  15

Leu Gly Asp Val Leu Pro Ala Glu Leu Pro Val Pro Leu Arg Glu Leu
            20                  25                  30

-continued

```
Asn Asp Pro Ala Arg Cys Glu Ala Ala Leu Leu Pro Tyr Leu Ala Trp
            35                  40                  45

Thr Arg Ser Val Asp Arg Trp Asp Pro Asp Trp Ser Asp Glu Ala Lys
 50                  55                  60

Arg Asn Ala Val Ala Thr Ser Phe Val Leu His Gln Arg Lys Gly Thr
 65                  70                  75                  80

Leu Thr Ala Leu Arg Gln Val Val Glu Pro Ile Gly Ala Leu Ser Glu
                 85                  90                  95

Val Thr Glu Trp Trp Gln Arg Ser Pro Leu Gly Val Pro Gly Thr Phe
            100                 105                 110

Glu Ile Thr Val Asp Val Ser Asp Arg Gly Ile Asp Glu Gly Thr Val
            115                 120                 125

Leu Glu Leu Glu Arg Leu Leu Asp Asp Val Arg Pro Val Ser Arg His
130                 135                 140

Leu Thr Arg Leu Asp Leu Arg Ile Thr Pro Val Ile Arg Ser Arg His
145                 150                 155                 160

Gly Leu Ala Val Thr Asp Gly Asp Thr Leu Glu Ile Phe Pro Trp Lys
                165                 170                 175

Gln
```

<210> SEQ ID NO 2
<211> LENGTH: 701
<212> TYPE: PRT
<213> ORGANISM: Pseudomonas aeruginosa

<400> SEQUENCE: 2

```
Met Thr Thr Asn Thr Pro Lys Tyr Gly Gly Leu Leu Thr Asp Ile Gly
 1               5                  10                  15

Ala Ala Leu Ala Ala Ala Ser Ala Ala Gly Lys Lys Trp Gln Pro
            20                  25                  30

Thr His Met Leu Ile Gly Asp Ala Gly Gly Ala Pro Gly Asp Thr Pro
            35                  40                  45

Asp Pro Leu Pro Ser Ala Ala Gln Lys Ser Leu Ile Asn Gln Arg His
 50                  55                  60

Arg Ala Gln Leu Asn Arg Leu Phe Val Ser Asp Lys Asn Ala Asn Thr
 65                  70                  75                  80

Leu Val Ala Glu Val Val Leu Pro Val Glu Val Gly Gly Phe Trp Ile
                 85                  90                  95

Arg Glu Ile Gly Leu Gln Asp Ala Asp Gly Lys Phe Val Ala Val Ser
            100                 105                 110

Asn Cys Pro Pro Ser Tyr Lys Ala Ala Met Glu Ser Gly Ser Ala Arg
            115                 120                 125

Thr Gln Thr Ile Arg Val Asn Ile Ala Leu Ser Gly Leu Glu Asn Val
130                 135                 140

Gln Leu Leu Ile Asp Asn Gly Ile Ile Tyr Ala Thr Gln Asp Trp Val
145                 150                 155                 160

Lys Glu Lys Val Ala Ala Asp Phe Lys Gly Arg Lys Ile Leu Ala Gly
                165                 170                 175

Asn Gly Leu Val Gly Gly Gly Asp Leu Ser Ala Asp Arg Ser Ile Gly
            180                 185                 190

Leu Ala Pro Ser Gly Val Thr Ala Gly Ser Tyr Arg Ser Val Thr Val
            195                 200                 205

Asn Ala Asn Gly Val Val Thr Gln Gly Ser Asn Pro Thr Thr Leu Ala
210                 215                 220
```

```
Gly Tyr Ala Ile Gly Asp Ala Tyr Thr Lys Ala Asp Thr Asp Gly Lys
225                 230                 235                 240

Leu Ala Gln Lys Ala Asn Lys Ala Thr Thr Leu Ala Gly Tyr Gly Ile
            245                 250                 255

Thr Asp Ala Leu Arg Val Asp Gly Asn Ala Val Ser Ser Ser Arg Leu
        260                 265                 270

Ala Ala Pro Arg Ser Leu Ala Ala Ser Gly Asp Ala Ser Trp Ser Val
    275                 280                 285

Thr Phe Asp Gly Ser Ala Asn Val Ser Ala Pro Leu Ser Leu Ser Ala
290                 295                 300

Thr Gly Val Ala Ala Gly Ser Tyr Pro Lys Val Thr Val Asp Thr Lys
305                 310                 315                 320

Gly Arg Val Thr Ala Gly Met Ala Leu Ala Ala Thr Asp Ile Pro Gly
                325                 330                 335

Leu Asp Ala Ser Lys Leu Val Ser Gly Val Leu Ala Glu Gln Arg Leu
                340                 345                 350

Pro Val Phe Ala Arg Gly Leu Ala Thr Ala Val Ser Asn Ser Ser Asp
            355                 360                 365

Pro Asn Thr Ala Thr Val Pro Leu Met Leu Thr Asn His Ala Asn Gly
    370                 375                 380

Pro Val Ala Gly Arg Tyr Phe Tyr Ile Gln Ser Met Phe Tyr Pro Asp
385                 390                 395                 400

Gln Asn Gly Asn Ala Ser Gln Ile Ala Thr Ser Tyr Asn Ala Thr Ser
                405                 410                 415

Glu Met Tyr Val Arg Val Ser Tyr Ala Ala Asn Pro Ser Ile Arg Glu
                420                 425                 430

Trp Leu Pro Trp Gln Arg Cys Asp Ile Gly Gly Ser Phe Thr Lys Thr
            435                 440                 445

Thr Asp Gly Ser Ile Gly Asn Gly Val Asn Ile Asn Ser Phe Val Asn
    450                 455                 460

Ser Gly Trp Trp Leu Gln Ser Thr Ser Glu Trp Ala Ala Gly Gly Ala
465                 470                 475                 480

Asn Tyr Pro Val Gly Leu Ala Gly Leu Leu Ile Val Tyr Arg Ala His
                485                 490                 495

Ala Asp His Ile Tyr Gln Thr Tyr Val Thr Leu Asn Gly Ser Thr Tyr
                500                 505                 510

Ser Arg Cys Cys Tyr Ala Gly Ser Trp Arg Pro Trp Arg Gln Asn Trp
            515                 520                 525

Asp Asp Gly Asn Phe Asp Pro Ala Ser Tyr Leu Pro Lys Ala Gly Phe
    530                 535                 540

Thr Trp Ala Ala Leu Pro Gly Lys Pro Ala Thr Phe Pro Pro Ser Gly
545                 550                 555                 560

His Asn His Asp Thr Ser Gln Ile Thr Ser Gly Ile Leu Pro Leu Ala
                565                 570                 575

Arg Gly Gly Leu Gly Ala Asn Thr Ala Ala Gly Ala Arg Asn Asn Ile
                580                 585                 590

Gly Ala Gly Val Pro Ala Thr Ala Ser Arg Ala Leu Asn Gly Trp Trp
            595                 600                 605

Lys Asp Asn Asp Thr Gly Leu Ile Val Gln Trp Met Gln Val Asn Val
    610                 615                 620

Gly Asp His Pro Gly Gly Ile Ile Asp Arg Thr Leu Thr Phe Pro Ile
625                 630                 635                 640
```

```
Ala Phe Pro Ser Ala Cys Leu His Val Val Pro Thr Val Lys Glu Val
                645                 650                 655

Gly Arg Pro Ala Thr Ser Ala Ser Thr Val Thr Val Ala Asp Val Ser
            660                 665                 670

Val Ser Asn Thr Gly Cys Val Ile Val Ser Ser Glu Tyr Tyr Gly Leu
        675                 680                 685

Ala Gln Asn Tyr Gly Ile Arg Val Met Ala Ile Gly Tyr
    690                 695                 700
```

<210> SEQ ID NO 3
<211> LENGTH: 386
<212> TYPE: PRT
<213> ORGANISM: Pseudomonas aeruginosa

<400> SEQUENCE: 3

```
Met Ser Phe Phe His Gly Val Thr Val Thr Asn Val Asp Ile Gly Ala
1               5                   10                  15

Arg Thr Ile Ala Leu Pro Ala Ser Ser Val Ile Gly Leu Cys Asp Val
            20                  25                  30

Phe Thr Pro Gly Ala Gln Ala Ser Ala Lys Pro Asn Val Pro Val Leu
        35                  40                  45

Leu Thr Ser Lys Lys Asp Ala Ala Ala Phe Gly Ile Gly Ser Ser
50                  55                  60

Ile Tyr Leu Ala Cys Glu Ala Ile Tyr Asn Arg Ala Gln Ala Val Ile
65                  70                  75                  80

Val Ala Val Gly Val Glu Ala Ala Glu Thr Pro Glu Ala Gln Ala Ser
                85                  90                  95

Ala Val Ile Gly Gly Val Ser Ala Ala Gly Glu Arg Thr Gly Leu Gln
            100                 105                 110

Ala Leu Leu Asp Gly Lys Ser Arg Phe Asn Ala Gln Pro Arg Leu Leu
        115                 120                 125

Val Ala Pro Gly His Ser Ala Gln Gln Ala Val Ala Thr Ala Met Asp
    130                 135                 140

Gly Leu Ala Glu Lys Leu Arg Ala Ile Ala Ile Leu Asp Gly Pro Asn
145                 150                 155                 160

Ser Thr Asp Glu Ala Ala Val Ala Tyr Ala Lys Asn Phe Gly Ser Lys
                165                 170                 175

Arg Leu Phe Met Val Asp Pro Gly Val Gln Val Trp Ser Ala Thr
            180                 185                 190

Asn Ala Ala Arg Asn Ala Pro Ala Ser Ala Tyr Ala Ala Gly Leu Phe
        195                 200                 205

Ala Trp Thr Asp Ala Glu Tyr Gly Phe Trp Ser Ser Pro Ser Asn Lys
    210                 215                 220

Glu Ile Lys Gly Val Thr Gly Thr Ser Arg Pro Val Glu Phe Leu Asp
225                 230                 235                 240

Gly Asp Glu Thr Cys Arg Ala Asn Leu Leu Asn Asn Ala Asn Ile Ala
                245                 250                 255

Thr Ile Ile Arg Asp Asp Gly Tyr Arg Leu Trp Gly Asn Arg Thr Leu
            260                 265                 270

Ser Ser Asp Ser Lys Trp Ala Phe Val Thr Arg Val Arg Thr Met Asp
        275                 280                 285

Leu Val Met Asp Ala Ile Leu Ala Gly His Lys Trp Ala Val Asp Arg
    290                 295                 300

Gly Ile Thr Lys Thr Tyr Val Lys Asp Val Thr Glu Gly Leu Arg Ala
305                 310                 315                 320
```

-continued

```
Phe Met Arg Asp Leu Lys Asn Gln Gly Ala Val Ile Asn Phe Glu Val
            325                 330                 335

Tyr Ala Asp Pro Asp Leu Asn Ser Ala Ser Gln Leu Ala Gln Gly Lys
            340                 345                 350

Val Tyr Trp Asn Ile Arg Phe Thr Asp Val Pro Pro Ala Glu Asn Pro
        355                 360                 365

Asn Phe Arg Val Glu Val Thr Asp Gln Trp Leu Thr Glu Val Leu Asp
        370                 375                 380

Val Ala
385

<210> SEQ ID NO 4
<211> LENGTH: 167
<212> TYPE: PRT
<213> ORGANISM: Pseudomonas aeruginosa

<400> SEQUENCE: 4

Met Ile Pro Gln Thr Leu Thr Asn Thr Asn Leu Phe Ile Asp Gly Val
1               5                   10                  15

Ser Phe Ala Gly Asp Val Pro Ser Leu Thr Leu Pro Lys Leu Ala Val
            20                  25                  30

Lys Thr Glu Gln Tyr Arg Ala Gly Gly Met Asp Ala Pro Val Ser Ile
            35                  40                  45

Asp Met Gly Leu Glu Ala Met Glu Ala Lys Phe Ser Thr Asn Gly Ala
        50                  55                  60

Arg Arg Glu Ala Leu Asn Phe Phe Gly Leu Ala Asp Gln Ser Ala Phe
65                  70                  75                  80

Asn Gly Val Phe Arg Gly Ser Phe Lys Gly Gln Lys Gly Ala Ser Val
            85                  90                  95

Pro Val Val Ala Thr Leu Arg Gly Leu Leu Lys Glu Val Asp Pro Gly
            100                 105                 110

Asp Trp Lys Ala Gly Glu Lys Ala Glu Phe Lys Tyr Ala Val Ala Val
            115                 120                 125

Ser Tyr Tyr Lys Leu Glu Val Asp Gly Arg Glu Val Tyr Glu Ile Asp
        130                 135                 140

Pro Val Asn Gly Val Arg Ala Ile Asn Gly Val Asp Gln Leu Ala Gly
145                 150                 155                 160

Met Arg Asn Asp Leu Gly Leu
            165
```

COMPOSITIONS AND METHODS FOR REMEDIATION OF SULFATE REDUCING PROKARYOTES

CROSS-REFERENCE TO RELATED APPLICATIONS

This patent application is a national stage of International Patent Application No. PCT/US2019/014061, filed Jul. 6, 2018, which claims the benefit of the priority of U.S. Provisional Patent Application No. 62/531,568, filed Jul. 12, 2017. The entire content of the foregoing applications are incorporated herein by reference, including all text, tables, drawings, and sequences.

RELATED PATENT APPLICATIONS

This patent application claims the benefit of U.S. Provisional Patent Application No. 62/531,568, filed Jul. 12, 2017. The entire content of the foregoing application is incorporated herein by reference, including all text, tables, drawings, and sequences.

DEPOSITED BIOLOGICAL MATERIAL

A novel *Pseudomonas aeruginosa* bacterial strain was deposited under the Budapest Treaty on the International Recognition of the Deposit of Material for the Purposes of Patent Procedure on Jun. 28, 2017 with the American Type Culture Collection, 10801 University Boulevard, Manassas, Va., 20110, USA and assigned Accession No. PTA-124262. This deposit is discussed herein.

INCORPORATION—BY REFERENCE OF MATERIAL SUBMITTED IN ELECTRONIC FORM

Applicant hereby incorporates by reference the Sequence Listing material filed in electronic form herewith. This file is labeled 80935-WO-PCT_ST25.txt", was created on Jul. 6, 2018, and is 13 KB in size.

BACKGROUND OF THE INVENTION

Microbiologically influenced corrosion (MIC) and souring are primary mechanisms for degradation of infrastructure and deterioration of product quality in oil and gas operations. Considerable microbial population diversity exists in different oil and gas production environments, particularly water-containing (i.e., aqueous) environments. Sulfate reducing prokaryotes (SRPs) are single-celled organisms that do not have a nucleus or any other membrane-bound organelles, e.g., bacteria, cyanobacteria, and archaea. Various SRP species of *Desulfovibrio* are a primary causative agent of souring and MIC, because SRPs consume hydrogen, produce corrosive hydrogen sulfide, and induce formation of ferrous sulfide. Iron-reducing bacteria (IRB), such as *Shewanella oneidensis* and *Geobacter sulfurreducens*, promote corrosion by reductively dissolving the protective ferric oxide coat that forms on the steel surface. Other reported microorganisms associated with corrosion include acid-producing bacteria (APB), such as *Acetobacterium carbinolicum*, that produce corrosive acids, such as acetate and butyrate, to induce corrosion. Still other unwanted microorganisms in this environment include methane-producing archaea, such as *Methanoplanus petrolearius*. The oil and gas industry currently uses a host of biocides to treat microorganisms that cause corrosion and souring. Both oxidizing (chlorine, chloramines) or non-oxidizing chemical biocides (amine-type compounds, anthraquinones and aldehydes) are widely applied within the industry to control microbial populations. Biocide application is not always effective, possibly due to the different identities and physiologies of microorganisms to be controlled in different systems. In addition to their poor effectiveness, the environmental impacts of those chemical biocides are generally considered negative.

Some bacterial strains indigenous to oil fields produce natural antimicrobial substances to combat different surrounding oil field microbial populations. These antimicrobial substances are usually small molecules, including but not limited to bacteriocins, secreted enzymes such as proteases, RNA-degrading enzymes or cell wall lytic enzymes. Some of these substances are active only against the same or closely related species while others have a broad activity spectrum. See, e.g., US published patent application No. 2014/0090833 which describes applying a range of purified bacteriocins and International Application No. WO2016/081239. For example, some *Bacillus* strains were isolated from oil fields and their capabilities for producing antimicrobial substances against other *Bacillus* strains and SRPs were reported (Korenblum E, et al. 2005 Production of antimicrobial substances by *Bacillus subtilis* LFE-1, *B. firmus* HO-1 and *B. licheniformis* T6-5 isolated from an oil reservoir in Brazil. *J Appl Microbiol.;* 98(3):667-75).

The problems and need for remediation of SRPs in oil and gas operation waters and in oil and gas reservoirs (production of hydrogen sulfide) are well described in U.S. Pat. Nos. 8,168,419 and 8,252,576, the disclosures of which are incorporated herein by reference. See, also, Australian patent publication 2009356541 and Chinese Application No. 105154464.

A continuing need in the art exists for less toxic and more effective tools and methods for controlling microbial influenced corrosion and souring of oil and gas fields.

SUMMARY OF THE INVENTION

In one embodiment, an isolated *Pseudomonas aeruginosa* bacterium, ATCC Accession No. PTA-124262 and progeny or derivatives thereof is provided.

In another aspect, a composition having broad range killing activity against SRPs comprising *Pseudomonas aeruginosa* bacterium, ATCC Accession No. PTA-124262 and progeny or derivatives thereof and a suitable carrier.

In another aspect, a bacteriocin isolated from *Pseudomonas aeruginosa* bacterium, ATCC Accession No. PTA-124262 and progeny or derivatives thereof is provided.

In still another aspect, a composition comprises a bacteriocin isolated from *Pseudomonas aeruginosa* bacterium, ATCC Accession No. PTA-124262 and progeny or derivatives thereof and a suitable carrier.

In a further aspect, a method of controlling unwanted prokaryotes in an oil or gas field environment or treatment fluid comprises contacting the environment or fluid with an amount of *Pseudomonas aeruginosa* bacterium, ATCC Accession No. PTA-124262 and progeny or derivatives thereof effective to produce bacteriocin in situ virulent for the unwanted prokaryotes, e.g., bacteria.

In yet another aspect, a method of controlling unwanted prokaryotes in an oil or gas field environment or treatment fluid comprises contacting the environment or fluid with an effective amount of a bacteriocin isolated from *Pseudomonas aeruginosa* bacterium, ATCC Accession No. PTA- 124262 and progeny or derivatives thereof, wherein said bacteriocin is virulent for the unwanted prokaryotes, e.g., bacteria.

In yet another aspect, a method of controlling unwanted prokaryotes in an oil or gas field environment or treatment fluid involves adding to said environment or fluid an effective amount of the whole cell bacterium of, or bacteriocin produced from, *Pseudomonas aeruginosa* bacterium, ATCC Accession No. PTA-124262 and progeny or derivatives thereof. These compositions can contain whole cell or bacteriocin from other microorganisms. Such compositions can be added together or sequentially to the aqueous systems.

Still other aspects and advantages of these compositions and methods are described further in the following detailed description of the preferred embodiments thereof.

DETAILED DESCRIPTION

Methods and compositions are described for mitigation of souring and MIC in oil and gas pipeline environments, including aqueous (water-containing) environments, as well as for other uses. Composition and methods for remediation of unwanted prokaryotes, particularly SRPs, in aqueous environments in oil and gas pipelines are provided by introduction of whole cells from a novel *Pseudomonas aeruginosa* strain ATCC PTA-124262, recovered from oil and gas operation waste waters and/or bacteriocin produced by that strain. The use of such methods and compositions are designed to reduce hydrogen sulfide production and associated souring and MIC. The exposure of oil and gas pipelines to these viable bacterial cells that produce and secrete chemicals (bacteriocins) that inhibit the growth of SRPs is a valuable tool for such remediation.

Exposure of oil and gas pipelines to the anti-SRP *Pseudomonas* strains leads to co-colonization of new and pre-existing SRP-containing biofilms along the inner surfaces of the pipelines. The close proximity between SRPs and the anti-SRP *Pseudomonas* strains induce the *Pseudomonas* strains to produce anti-SRP bacteriocins in order to achieve a competitive advantage.

Definitions and Components of the Compositions and Methods

Technical and scientific terms used herein have the same meaning as commonly understood by one of ordinary skill in the art to which this invention belongs and by reference to published texts, which provide one skilled in the art with a general guide to many of the terms used in the present application. The definitions contained in this specification are provided for clarity in describing the components and compositions herein and are not intended to limit the claimed invention. The following terms are used throughout the specification.

By "bacteriocins" is meant proteinaceous (peptide or proteins) anti-microbial toxins normally produced by bacteria to inhibit the growth of taxonomically similar microbial competitors in the nearby environment. Productions of bacteriocins both by Gram positive bacteria (such as lactic acid bacteria or *Bacillus*), and by Gram negative bacteria (many members of Enterobacteriaceae family, such as *Escherichia coli*), have been documented. Some of the documented bacteriocins exhibit a broad inhibition spectrum covering many members of Gram positive and Gram negative bacteria. The bacteriocin of ATCC Accession No. PTA-124262 inhibits growth of the SRPs, thereby reducing sulfide production and associated souring and MIC. Bacteriocins showing activity against different strains of SRPs have great potential for environmental applications as natural biocides in oil and gas industries, among others.

The term "unwanted prokaryote," as used herein, refers to single-celled organisms that do not have a nucleus or any other membrane-bound organelles, e.g., bacteria, cyanobacteria, and archaea. These prokaryotes include the strain(s) of prokaryotes, e.g., bacteria, specifically targeted for control by the invention described herein. Typically, but not necessarily, the unwanted prokaryotes are targeted for control because of interference with reactions or processes, such as in the case of unwanted SRPs and/or IRBs in oil and gas drilling and in production waters such as fracturing water, produced water and water. The unwanted prokaryotes need not necessarily be known, isolated, or identified; the sole defining characteristic is that it is the organism(s) desired to be controlled. This invention provides for reduction of invasive prokaryotes and other unwanted and problematic prokaryotes, e.g., SRPs and sulfate-reducing bacteria.

By "oil and gas field environments" or "oil and gas aqueous environments" is meant the fluids naturally occurring in the well itself or any type of fluid employed in a hydrocarbon recovery operation such as pipeline operations, well servicing operations, upstream exploration and production operations, downstream refining, processing, storage and transportation applications, and sterilization of flowback fluids. Such environments include drilling fluids, lost circulation fluids, stimulation fluids, sand control fluids, completion fluids, acidizing fluids, scale inhibiting fluids, water-blocking fluids, clay stabilizer fluids, fracturing fluids, frac-packing fluids, gravel packing fluids, wellbore strengthening fluids, acidizing fluids, sag control fluids, any flow-back fluid, which is a non-hydrocarbon containing fluid that flows from the well to the surface following treatment with another fluid, or wastewater.

By "carrier" as used herein includes, but is not limited to, aqueous-based fluids, such as fresh water, seawater, saltwater, or brine (e.g., water containing or saturated with one or more dissolved salts) and any combination thereof. A carrier may also be an aqueous-miscible fluid, such as alcohols, e.g., methanol, ethanol, n-propanol, isopropanol, n-butanol, sec-butanol, isobutanol, and t-butanol; glycerins; glycols; e.g., polyglycols, propylene glycol, and ethylene glycol; polyglycol amines; polyols; any derivative thereof; any in combination with salts, e.g., sodium chloride, calcium chloride, calcium bromide, zinc bromide, potassium carbonate, sodium formate, potassium formate, cesium formate, sodium acetate, potassium acetate, calcium acetate, ammonium acetate, ammonium chloride, ammonium bromide, sodium nitrate, potassium nitrate, ammonium nitrate, ammonium sulfate, calcium nitrate, sodium carbonate, and potassium carbonate. Combinations of one or more aqueous-miscible fluid with an aqueous-based fluid may also serve as carriers for the compositions described herein. Still other suitable carriers include emulsions, such as water-in-oil emulsions or oil-in-water emulsions, which are described in US2014/0090833, incorporated by reference herein.

By "additive" is meant pH adjuster or buffering agent, a carbon source, and glycerol, as well as any necessary reagents for cryopreservation until time of use. In one embodiment, the purified or partially purified bacteriocin is stable in just a buffer solution. In another embodiment, to stabilize a formulation containing whole cells, the formulation can include a salt, buffer to maintain pH, optionally a low level of a carbon source, and optionally glycerol.

"Effective amount" as used herein means an amount of whole cell sufficient to produce bacteriocin in sufficient concentration to cause a detectable reduction in, or killing of, targeted unwanted prokaryotes, e.g., bacteria. The effective amount can also be expressed in the amount of bacteriocin sufficient to cause a detectable reduction in, or killing of, targeted unwanted prokaryotes (e.g., SRPs). In some embodiments, the effective amount/concentration of whole cells of ATCC Accession No. PTA-124262 in the indicated oil and gas environment fluid is a concentration at least comparable to the level of SRPs present in the indicated environment. In one embodiment, an effective amount is at least $1\times10^3$, $1\times10^4$, $1\times10^5$, $1\times10^6$, $1\times10^7$, $1\times10^8$, or $1\times10^9$ colony forming units (cfu)/mL. In one embodiment, an effective amount is at least $1\times10^6$ cfu/ml. Higher or lower concentrations can also be employed. Similar amounts of other whole cell bacteria demonstrating anti-SRP activity may be combined with similar or smaller amounts of ATCC Accession No. PTA-124262, in the event of synergistic anti-SRP effect.

In some embodiments, the "effective amount" of bacteriocin in the indicated oil and gas environment fluid is an amount at least 0.1, 0.2, 0.3, 0.4, 0.5, 0.6, 0.7, 0.8, 0.9, 1, 5, 10, 30, 50, 80, or 100 ppm. In one embodiment, the dose is about 1 ppm. In some embodiments, the effective amount of bacteriocin in the indicated oil and gas environment fluid is an amount at least 0.1, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290 or about 300 mg/ml. Higher or lower concentrations can also be employed. Similar amounts of other bacteriocins demonstrating anti-SRP activity may be combined with similar or smaller amounts of ATCC Accession No. PTA-124262 bacteriocin, in the event of synergistic anti-SRP effect.

The phrase "anti-SRP effect" or "anti-SRP activity" means the ability to interfere with or reduce the propagation of functional SRPs. In another embodiment, anti-SRP activity means the ability to kill SRPs.

The words "comprise", "comprises", and "comprising" are to be interpreted inclusively rather than exclusively, i.e., to include other unspecified components or process steps. The words "consist", "consisting", and its variants, are to be interpreted exclusively, rather than inclusively, i.e., to exclude components or steps not specifically recited.

The terms "a" or "an" refers to one or more. For example, "an expression cassette" is understood to represent one or more such cassettes. As such, the terms "a" (or "an"), "one or more," and "at least one" are used interchangeably herein.

As used herein, the term "about" means a variability of plus or minus 10% from the reference given, unless otherwise specified.

Compositions

In one embodiment, a newly discovered strain of *Pseudomonas aeruginosa* bacteria produces a bacteriocin in situ having broad killing range for SRPs. In one embodiment, the newly isolated *P. aeruginosa* was deposited on Jun. 28, 2017 under Accession No. PTA-124262 with the American Type Culture Collection, located at 10801 University Boulevard, Manassas, Va. 20110 USA. As described in the examples below, this novel Gram negative, *Pseudomonas* strain was isolated from an oil and gas environment, i.e., from oil and gas field wastewater. This strain has been shown to inhibit SRP growth in zone-of-inhibition assays on agar plates. The anti-SRP activity was found to be associated with an R-type pyocin (*Pseudomonas* bacteriocin with a bacteriophage tail structure).

In another embodiment, progeny of ATCC Accession No. PTA-124262 and/or derivatives thereof are provided and can be used in the compositions and methods described herein. By "progeny" is meant repeated generations of ATCC Accession No. PTA-124262 resulting from repeated culturing and including any mutations that occur naturally during culturing. By "derivatives" are meant progeny bacteria of the deposited microorganisms which carry mutations or deletions of amino acids or nucleotide bases which are created in the bacterial genome by genetic engineering or recombinant manipulation techniques.

In one embodiment, ATCC Accession No. PTA-124262 and progeny or derivatives carry naturally occurring or genetically manipulated proteins including tail fiber and tail tube proteins. The anti-SRP bacteriocin produced by ATCC Accession No. PTA-124262 is an R-type pyocin with the structure of a phage tail. The complex consists of about 130 copies of a FI tail sheath monomer SEQ ID NO: 3, with a length of 386 AA and a predicted weight of 41 kDa, and about 130 copies of a FII tail tube monomer SEQ ID NO: 4 with a length of 167 AA and a predicted weight of 18 kDa. The approximate predicted molecular weight of the entire pyocin is 7700 kDa. The anti-SRP activity of the bacteriocin is associated with the particular three dimensional structure/interaction of the associated tail fiber proteins. Altering these sequences is anticipated to alter or broaden the specificity of the bacteriocin. The tail fiber proteins SEQ ID NO: 1 and 2 are present at low copy number. The tail fiber proteins are involved in binding of the pyocin to a target cell, i.e. host range specificity. The major structural proteins aren't directly involved in host recognition.

Amino acid sequences for the two major structural proteins and two of the tail fiber proteins of the ATCC Accession No. PTA-124262 anti-SRP bacteriocin are:

```
contig00021_64327_64860 Phage tail fibers ~20 kDa:
                                         SEQ ID NO: 1
MSSRLLPPNRSSLERSLGDVLPAELPVPLRELNDPARCEAALLPYLAWTR

SVDRWDPDWSDEAKRNAVATSFVLHQRKGTLTALRQVVEPIGALSEVTEW

WQRSPLGVPGTFEITVDVSDRGIDEGTVLELERLLDDVRPVSRHLTRLDL

RITPVIRSRHGLAVTDGDTLEIFPWKQ contig00021_64862_66967 Phage tail fiber protein
~73 kDa
                                         SEQ ID NO: 2
MTTNTPKYGGLLTDIGAAALAAASAAGKKWQPTHMLIGDAGGAPGDTPDP

LPSAAQKSLINQRHRAQLNRLFVSDKNANTLVAEVVLPVEVGGFWIREIG

LQDADGKFVAVSNCPPSYKAAMESGSARTQTIRVNIALSGLENVQLLIDN

GIIYATQDWVKEKVAADFKGRKILAGNGLVGGGDLSADRSIGLAPSGVTA

GSYRSVTVNANGVVTQGSNPTTLAGYAIGDAYTKADTDGKLAQKANKATT

LAGYGITDALRVDGNAVSSSRLAAPRSLAASGDASWSVTFDGSANVSAPL

SLSATGVAAGSYPKVTVDTKGRVTAGMALAATDIPGLDASKLVSGVLAEQ

RLPVFARGLATAVSNSSDPNTATVPLMLTNHANGPVAGRYFYIQSMFYPD

QNGNASQIATSYNATSEMYVRVSYAANPSIREWLPWQRCDIGGSFTKTTD

GSIGNGVNINSFVNSGWWLQSTSEWAAGGANYPVGLAGLLIVYRAHADHI

YQTYVTLNGSTYSRCCYAGSWRPWRQNWDDGNFDPASYLPKAGFTWAALP

GKPATFPPSGHNHDTSQITSGILPLARGGLGANTAAGARNNIGAGVPATA
```

-continued
SRALNGWWKDNDTGLIVQWMQVNVGDHPGGIIDRTLTFPIAFPSACLHVV

PTVKEVGRPATSASTVTVADVSVSNTGCVIVSSEYYGLAQNYGIRVMAIG

Y contig00021_67458_68618 Phage tail sheath monomer
(FI tail sheath) ~41 kDa (~130 copies per tail)
                                          SEQ ID NO: 3
MSFFHGVTVTNVDIGARTIALPASSVIGLCDVFTPGAQASAKPNVPVLLT

SKKDAAAAFGIGSSIYLACEAIYNRAQAVIVAVGVEAAETPEAQASAVIG

GVSAAGERTGLQALLDGKSRFNAQPRLLVAPGHSAQQAVATAMDGLAEKL

RAIAILDGPNSTDEAAVAYAKNFGSKRLFMVDPGVQVWDSATNAARNAPA

SAYAAGLFAWTDAEYGFWSSPSNKEIKGVTGTSRPVEFLDGDETCRANLL

NNANIATIIRDDGYRLWGNRTLSSDSKWAFVTRVRTMDLVMDAILAGHKW

AVDRGITKTYVKDVTEGLRAFMRDLKNQGAVINFEVYADPDLNSASQLAQ

GKVYWNIRFTDVPPAENPNFRVEVTDQWLTEVLDVA contig00021_68631_69134 Phage major tail tube
protein (FII tail tube) ~18 kDa (~130 copies per
tail)
                                          SEQ ID NO: 4
MIPQTLTNTNLFIDGVSFAGDVPSLTLPKLAVKTEQYRAGGMDAPVSIDM

GLEAMEAKFSTNGARREALNFFGLADQSAFNGVFRGSFKGQKGASVPVVA

TLRGLLKEVDPGDWKAGEKAEFKYAVAVSYYKLEVDGREVYEIDPVNGVR

AINGVDQLAGMRNDLGL

Such proteins may be genetically manipulated or engineered to result in certain mutated proteins having desirable characteristics. Thus, proteins produced by the progeny and derivatives of ATCC Accession No. PTA-124262 include naturally occurring proteins, such as SEQ ID Nos 1-4, encoded by the genomic DNA or cDNA derived from the microorganism, as well as functional proteins (i.e., proteins that demonstrate the biological activity of the normally functioning protein SEQ ID Nos: 1, 2, 3 and/or 4, with mutations or modifications of its encoding DNA sequence or within its amino acid sequence. In another embodiment, such a functional protein can include mutations which cause the protein to perform its anti-SRP functions better than a "native" or endogenous sequence. In one embodiment, such a functional bacteriocin or one of its individual protein elements can be considered a normal or normally-functioning protein.

Also included in the use of the definitions of the bacteriocin protein and tail fiber proteins described herein include sequences which differ from the reference sequences SEQ ID NO: 1, 2, 3 and/or 4 by virtue of naturally occurring nucleic acid base or amino acid mutations or silent mutations that occur in, or among, a selected species, or amino acid sequences which differ by conservative amino acid replacements, or sequences having at least 90, at least 95 or at least 99 percent identity with the reference sequences SEQ ID NO: 1, 2, 3 and/or 4.

Thus, in one embodiment, the tail fiber or bacteriocin protein sequences of ATCC Accession No. PTA-124262 and progeny or derivatives include a variant which shares or comprises at least 70, at least 75%, at least 78% or at least 80% identity with SEQ ID NO: 1, 2, 3 or 4. In another embodiment, the tail fiber or bacteriocin protein sequences share at least 85% identity with a native protein produced by these bacteria. In another embodiment, the bacteriocin or tail fiber protein sequence shared at least 90% identity with a native bacteriocin or tail fiber protein sequence (i.e., SEQ ID NO: 1, 2, 3 or 4). In another embodiment, the bacteriocin or tail fiber protein(s) sequence shares at least 91% identity with a native bacteriocin or tail fiber protein(s). In another embodiment, the bacteriocin or tail fiber protein(s) sequence shares at least 92% identity with a native bacteriocin or tail fiber protein(s). In another embodiment, the bacteriocin or tail fiber protein(s) sequence shares at least 93% identity with a native bacteriocin or tail fiber protein(s). In another embodiment, the bacteriocin or tail fiber protein(s) sequence shares at least 94% identity with a native bacteriocin or tail fiber protein(s). In another embodiment, the bacteriocin or tail fiber protein(s) sequence shares at least 95% identity with a native bacteriocin or tail fiber protein(s). In another embodiment, the bacteriocin or tail fiber protein(s) sequence shares at least 96% identity with a native bacteriocin or tail fiber protein(s). In another embodiment, the bacteriocin or tail fiber protein(s) sequence shares at least 97% identity with a native bacteriocin or tail fiber protein(s). In another embodiment, the bacteriocin or tail fiber protein(s) sequence shares at least 98% identity with a native bacteriocin or tail fiber protein(s). In another embodiment, the bacteriocin or tail fiber protein(s) sequence shares at least 99% identity with a native bacteriocin or tail fiber protein(s) described herein. In a similar manner, the nucleotide sequences encoding the bacteriocin or tail fiber protein(s) of ATCC Accession No. PTA-124262 and its progeny or derivatives may share analogous percent identities over a stretch of contiguous nucleotide bases encoding the proteins.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 10 amino acids to about 300 amino acids, or a peptide fragment thereof. Percent identity may be readily determined for nucleotide sequences over the full-length nucleic acid sequence coding sequences or partial coding sequences, or non-coding sequences.

Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another method which provides at least the same level of identity or alignment as that provided by the referenced methods. See, e.g., J. D. Thomson et al, Nucl. Acids. Res., "A comprehensive comparison of multiple sequence alignments", 27(13):2682-2690 (1999).

The bacteriocin or tail fiber protein(s) of the deposited microorganism or its progeny or derivatives may also be "optimized" or "codon-optimized". The bacteriocin or tail fiber protein(s) can be encoded by a DNA sequence which differs from the native or naturally occurring sequence, such as that of SEQ ID NO: 1, 2, 3 or 4, by codon changes that make silent, conservative or non-conservative amino acid changes, or amino acid insertions or deletions in the protein(s). These changes may increase protein production and/or enhance protein conformation and stability. Synonymous codon changes or codon changes resulting in conservative amino acid changes, or insertions or deletions can increase protein production and/or enhance protein conformation and stability.

Creating bacteriocins or tail fiber proteins that differ from the native sequences can be accomplished by various different methods. Optimization may be performed using methods which are available on-line, published methods, or a company which provides codon optimizing services (see e.g., in International Patent Application Pub. No. WO 2015/012924, which is incorporated by reference herein). Briefly, the nucleic acid sequence encoding the desired protein is modified with synonymous codon sequences. Suitably, the entire length of the open reading frame (ORF) for the bacteriocin or tail fiber protein(s) is modified. However, in some embodiments, only a fragment of the ORF may be altered. By using one of these methods, one can produce a nucleic acid fragment of a codon-optimized coding region which encodes the bacteriocin or tail fiber protein. Such modifications or synthesis of bacteriocins and/or tail fiber proteins can be performed using standard and routine molecular biological manipulations well known to those of ordinary skill in the art. See, Green and Sambrook et al, "Molecular Cloning. A Laboratory Manual", Fourth Edition, 2012 by Cold Spring Harbor Laboratory Press, Cold Spring Harbor, N.Y., among other texts.

It is anticipated that several other gene products are required for full transcription, assembly, function and specificity of the anti-SRP bacteriocin.

Compositions described herein, in one embodiment, have broad range killing activity against SRPs and comprise, in one embodiment, whole cell *Pseudomonas aeruginosa* bacterium, ATCC Accession No. PTA-124262 and progeny or derivatives thereof and a suitable carrier. In another embodiment, such a composition can also include at least one or more additional bacteria that is or are useful in reducing corrosion or souring. Among such bacteria include other strains of *Pseudomonas aeruginosa*. In another embodiment strains of *Thauera aminoaromatica* may be included in the composition. In still another embodiment, strains of the bacteria *Ideonella* may be employed. Still other bacteria known or found to produce anti-SRP bacteriocins or to compete with IRBs, APBs, and the like present in oil and gas field environments may be combined with ATCC Accession No. PTA-124262 in a suitable composition. Other known bacterial strains known by the art to be suitable for anti-souring and anti-corrosion effect may also be added to the compositions described herein.

In still another embodiment, the compositions containing ATCC Accession No. PTA-124262 may also contain additional suitable bacteriocin protein(s) rather than additional whole cell bacteria, for such use. See, e.g., the bacteriocin described in US published patent application No. 2014/0090833, incorporated by reference herein.

Compositions having broad range killing activity against SRPs comprise, in another embodiment, a bacteriocin produced from the bacterium ATCC Accession No. PTA-124262 and progeny or derivatives thereof as described above, and a suitable carrier. In another embodiment, such a composition can also include at least one or more additional bacteriocin(s) that is/are useful in reducing corrosion or souring. Among such bacteriocins are included those produced by other strains of *Pseudomonas aeruginosa*, such as pyocin R1, R2, R3, R4, S1, S2, S3, S4, S5, F1, F2, F3, AP41, and AR41, which may have anti-corrosion or anti-SRP activity. In another embodiment strains of *Thauera aminoaromatica* may be included in the composition. In still another embodiment, bacteriocin produced by strains of the bacteria *Ideonella* may be employed. Still other bacteriocins known to be toxic to IRBs, APBs, and the like present in oil and gas field environments may be combined with the bacteriocin produced by ATCC Accession No. PTA-124262 in a suitable composition. Other known bacteriocins known by the art to be suitable for anti-souring and anti-corrosion effect may also be added to the compositions described herein, such as those described in US published patent application No. 2014/0090833, incorporated by reference herein. Other bacteria or bacteriocins isolated therefrom having a corrosion protective potential may be employed in concert with whole cell bacterium ATCC Accession No. PTA-124262 and progeny or derivatives thereof, including without limitation, *Bacillus thuringiensis*-SN8 (Bano, Arjumand Shah, and Javed Iqbal Qazi. "Soil buried Mild Steel Corrosion by *Bacillus cereus*-SNB4 and its Inhibition by *Bacillus thuringiensis*-SN8." Pakistan J. Zool 43.3 (2011): 555-562); *Bacillus subtilis*-LFE-1, *Bacillus firmus*-H2O-1 and *Bacillus licheniformis*-T6-5 (Korenblum, E., et al. "Production of antimicrobial substances by *Bacillus subtilis* LFE-1, *B. firmus* H2O-1 and *B. licheniformis* T6-5 isolated from an oil reservoir in Brazil." Journal of Applied Microbiology 98.3 (2005): 667-675); *Bacillus* sp. H2O-1 (Korenblum, Elisa, et al. "Purification and characterization of a surfactin-like molecule produced by *Bacillus* sp. H2O-1 and its antagonistic effect against sulfate reducing bacteria." BMC microbiology 12.1 (2012): 252).

In one embodiment, such whole cell ATCC Accession No. PTA-124262 only may be prepared for use in one or more of the carriers described and defined above for a variety of uses. In another embodiment, mixtures of ATCC Accession No. PTA-124262 with such other bacteria as mentioned above may be prepared for use in one or more of the carriers described and defined above for a variety of uses. In another embodiment, mixtures of ATCC Accession No. PTA-124262 cells with bacteriocin produced by the other above-mentioned bacteria may be prepared for use in one or more of the carriers described and defined above for a variety of uses. In still another embodiment bacteriocin and/or tail fiber protein (s) produced by and isolated from ATCC Accession No. PTA-124262, which may be mutated or modified as described above, may be prepared for use in one or more of the carriers described and defined above for a variety of uses. In another embodiment, mixtures of the bacteriocin of ATCC Accession No. PTA-124262 (naturally occurring and/or modified as described above) with other bacteriocins produced by other bacteria, may be prepared for use in one or more of the carriers described and defined above for a variety of uses. In still a further embodiment, mixtures of whole cell ATCC Accession No. PTA-124262 with its own or other bacteriocin compositions may be prepared for use in one or more of the carriers described and defined above for a variety of uses.

Such whole cell, bacteriocin or mixed whole cell and bacteriocin may be added to compositions for use or measured in situ in concentrations suitable to achieve their anti-SRP, anti-souring, anti-corrosion effect, as also defined herein.

Methods

The anti-SRP activity of *P. aeruginosa* ATCC Accession No. PTA-124262 is useful in diminishing the SRP population in mixed biofilms in which it is present. It is theorized that ATCC Accession No. PTA-124262 is an oilfield isolate that may have existed in close proximity to SRPs in the oilfield; and that bacteriocins are produced by bacteria to diminish other bacterial populations that exist in close proximity and that compete for the same/similar carbon sources (i.e. both can use lactate). Many bacteria in the environment exist within multi-species biofilm formations.

Treatment of pipelines and other oil and gas field environments, within oil drilling and natural gas fracking operations, with whole-cell ATCC Accession No. PTA-124262 co-colonizes new or pre-existing SRP-containing biofilms with an organism that has the effect of diminishing the SRP population within the biofilm. While complete biofilm dispersal may or may not occur during treatment, sulfide production is reduced, thereby reducing the risk of souring and MIC.

In one embodiment, the whole-cell *P. aeruginosa* ATCC Accession No. PTA-124262 compositions described herein having anti-SRP functionality, represent an inexpensive, differentiated technology that is not expected to encounter difficult regulatory hurdles.

Thus, in one embodiment, a method of controlling prokaryotes in an oil or gas field environment or treatment fluid, as defined above, comprises contacting the selected environment with an amount of *Pseudomonas aeruginosa* bacterium, ATCC Accession No. PTA-124262 and progeny or derivatives thereof effective to produce bacteriocin in situ which is virulent for the unwanted prokaryotes. The contacting occurs for a time sufficient to permit the bacterium to produce bacteriocin virulent for the unwanted prokaryotes or for the bacteriocin to kill the unwanted prokaryotes. As described above, the unwanted prokaryotes are SRPs, including without limitation one or more of *D. alaskensis, D. desulfuricans, D. longus*, or *D. vulgaris*. The method further comprises optionally contacting the selected oil and gas field environment with whole cell bacteria of another strain of *Pseudomonas aeruginosa*, or *Thauera aminoaromatica* or *Ideonella* that are capable of killing SRP.

In another embodiment, a method of controlling unwanted prokaryotes in an oil or gas field environment or treatment fluid, as defined above, comprises contacting the selected environment with an amount of a bacteriocin produced by *Pseudomonas aeruginosa* bacterium, ATCC Accession No. PTA-124262 and progeny or derivatives thereof. The bacteriocin are provided in effective amounts to be virulent for, reduce the number of, or kill, the unwanted prokaryotes. The method permits the bacteriocin virulent for the unwanted prokaryotes or for the bacteriocin to kill or substantially reduce the growth of the unwanted prokaryotes. As described above, in certain embodiments, the unwanted prokaryotes are SRPs, such as one or more of *D. alaskensis, D. desulfuricans, D. longus*, or *D. vulgaris*. The method further comprises optionally contacting the selected oil and gas field environment with bacteriocin produced by bacteria of another strain of *Pseudomonas aeruginosa*, or *Thauera aminoaromatica* or *Ideonella* that are capable of killing SRP.

In still further embodiments, the methods of reducing or controlling unwanted bacteria in oil and gas field environments comprises adding an effective amount of such whole cell ATCC Accession No. PTA-124262 only, or mixtures of ATCC Accession No. PTA-124262 with other bacteria, or bacteriocin only produced by and isolated from ATCC Accession No. PTA-124262, or mixtures of the bacteriocin of ATCC Accession No. PTA-124262 with other bacteriocins produced by other bacteria, or mixtures of whole cell ATCC Accession No. PTA-124262 with its own or other bacteriocin compositions as described herein to any oil or gas field environment or fluid.

The embodiment of the methods described herein use whole cell ATCC Accession No. PTA-124262 as a self-propagating biopesticide. These methods do not require costly bacteriocin purification. The use of the whole cell ATCC Accession No. PTA-124262 specifically targets SRPs (souring and MIC), without the need for added chelating agents, surfactants, etc. The whole cell method described herein represents a natural alternative that provides targeted biocontrol of MIC. From a regulatory perspective, use of the whole cell culture as a biopesticide is likely to be considered safer than chemical biocides. In one embodiment, the whole-cell bacterial treatment takes the form of a native, environmental isolate that has not undergone any genetic engineering. In addition, the biopesticidal activity propagates within the pipeline as a result of the propagation of the producing organism ATCC Accession No. PTA-124262.

Without being bound by theory, these methods exploit the strong tendency of microorganisms to exist within mixed biofilms in the environment. It is hypothesized that, although *Pseudomonas* ATCC Accession No. PTA-124262 and SRPs are not very similar taxonomically, this isolate produces an anti-SRP bacteriocin because it co-existed with SRPs in the oilfield environment and evolved an anti-SRP bacteriocin as a self-defense mechanism. While the trigger for turning on the bacteriocin expression is unknown, it is hypothesized that co-colonization of a biofilm by ATCC Accession No. PTA-124262 and SRPs promotes production or over-production of the anti-SRP bacteriocin.

In addition to the method steps defined above, other methods used in oil and gas operations to remediate unwanted prokaryotes that cause fouling, corrosion and reservoir souring ($H_2S$ production) may also employ the compositions containing ATCC Accession No. PTA-124262 or its bacteriocin described herein. A variety of suitable methods are described in U.S. Pat. No. 8,168,419 issued May 1, 2012 and U.S. Pat. No. 8,252,576, issued Aug. 28, 2012, the disclosures of which are incorporated herein by reference.

The compositions containing ATCC Accession No. PTA-124262 or its bacteriocin may be added to bacteriophage as well as other biocides. Since the bacteria in oil and gas wells are diverse, the remediation of a dominant strain may allow a less dominant strain to become dominant. In such case the less dominant may not be killed by the initially applied biocide composition (cocktail) used so that the cocktail composition is changed to remediate the dynamic changing population of unwanted prokaryotes. The change is effected base on monitored analysis or timed sequence.

A method of accomplishing such dynamic behavior is described in U.S. published application 2014/0273159, published, Sep., 18, 2014, for staged bacteriophage. The same procedures and methods may be applied for the composition (whole cell or bacteriocin or mixed) described herein. The whole cell ATCC Accession No. PTA-124262 or its bacteriocin may be contained in cocktails with bacteriophage including those described in U.S. published application 2014/0273159, published Sep. 18, 2014, the disclosure of which is incorporated herein by reference.

In one embodiment, a process for control of a broad range of target bacteria comprises culturing a dominant group of bacteria in a mixed bacteria solution. A composition containing ATCC Accession No. PTA-124262 which produces its bacteriocin in situ, or a composition containing the bacteriocin isolated from ATCC Accession No. PTA-124262 as well as other additional whole cell bacterial strains (e.g.,

*Pseudomonas aeruginosa, Thauera aminoaromatica* and *Ideonella*) and/or bacteriocin isolated therefrom are added to remove the dominant bacteria from the mix. The next dominant strain is cultured from the solution. An effective amount of whole cell ATCC Accession No. PTA-124262 and its bacteriocin with or without other bacteria or isolated bacteriocins from other bacterial strains is thereafter added to remove the next dominant bacteria. This series of steps is repeated to provide a set of ATCC Accession No. PTA-124262 progeny or derivatives thereof, and/or isolated bacteriocin that will reduce the dominant and sub-dominant bacteria. An effective amount of the ATCC Accession No. PTA-124262 progeny or derivatives or bacteriocin produced thereby that is/are so isolated in each step is thereafter applied as either a mixture or in sequential application to oil and gas field environments or treatment fluids containing a mixture of target bacteria of those found in each step of the above sequence.

It is further anticipated that the novel ATCC Accession No. PTA-124262 or its bacteriocin may be used for microbial control in environments, fluids and industries other than oil and gas production, e.g., for wastewater treatment in other contexts or even as additives to other products requiring microbial control.

EXAMPLES

The following examples disclose specific embodiments of the methods and compositions and should be construed to encompass any and all variations that become evident as a result of the teaching provided herein.

Example 1: Screening for Strains Producing Antimicrobial Substances Against Oil Field SRP Several thousand bacterial strains isolated from up to one hundred oil and gas samples were screened for their capabilities to produce substances that kill SRPs. The oil and gas samples include fracturing water, produced water, pit water, waste water collected mainly from North American production plants (oil and gas water systems). In detail, these samples were serial diluted and plated onto SRP selecting media plates. After incubation, the grown up individual colonies were picked and transferred onto a fresh plate. The colony leftovers on the original plate were killed by chloroform vapor.

The killed plates were overlaid with indicator bacterial lawns freshly made with different SRPs, including *D. alaskensis, D. desulfuricans, D. longus, D. vulgaris* and EBS.14 (a field isolate from Barnett Shale). After incubation, any zone of inhibition (ZOI) on the indicator SRP lawns was noted and the matching copy of the producing strain (transferred on a separate plate before killing) was purified and identified. ATCC Accession No. PTA-124262 was evaluated by 16S rDNA sequencing as *Pseudomonas aeruginosa*. The antimicrobial substance produced by this strain showed broad killing spectrum against 34 of 45 different SRP strains isolated from oil and gas fields.

Example 2: Preparation of Bacteriocin Extract from *Pseudomonas aeruginosa* EC42.15

A single colony of *Pseudomonas aeruginosa* EC42.15 ATCC Accession No. PTA-124262 was inoculated into 10 mL tryptic soy broth (TSB) and the culture was incubated overnight at 30° C. with shaking at 50 rpm. An aliquot of the overnight culture was transferred into a larger volume of TSB, using a 2% (v/v) inoculation level. The larger culture was incubated (30° C., 50-100 rpm) and the culture density was monitored until an $OD_{600}$ of about 0.4 was reached. Mitomycin C was then added to the culture to a final level of 1 µg/mL. Incubation (30° C., 50 rpm) was continued for an additional 18 hrs. Cells were collected by centrifugation at 11,000×g. The clarified supernatant (bacteriocin extract) was sterile-filtered and refrigerated.

The anti-SRP activity of the bacteriocin extract was partially purified using an ultrafiltration unit. The bacteriocin extract was passed through a 300 kDa molecular weight cut-off membrane, while stirring under an external pressure of 10 psi nitrogen. Ultrafiltration continued until the retentate volume was 10% of the starting volume. The retentate, which contained the anti-SRP activity, was desalted by diluting to the original volume in 10 mM Tris-Cl, pH 7.5, and repeating the concentration step. The partially purified bacteriocin extract was stored refrigerated.

Example 3: Characterization and Production of the Antimicrobial Substances Produced by *P. aeruginosa* ATCC Accession No. PTA-124262

The genome of *P. aeruginosa* ATCC Accession No. PTA-124262 was sequenced. The complete bioinformatics analysis of the genome sequence identified DNA regions coding putative antimicrobial proteins, SEQ ID Nos: 1, 2, 3 and 4. These antimicrobial proteins were partially purified from the culture supernatant and the specific activity against SRPs was determined as described above. It is anticipated that further modification of these proteins will permit efficient production for application in controlling SRP of oil and gas industries. The antimicrobial proteins can be expressed in their native host, i.e., ATCC Accession No. PTA-124262, or expressed in a different bacterial host for maximum production rate. Multiple antimicrobial proteins with different SRP killing spectrums can be combined for broader SRP control in the oil and gas industry.

The bacteriocin of ATCC Accession No. PTA-124262 is an R-type pyocin with a phage tail structure. The complex consists of about 130 copies of a FI tail sheath monomer SEQ ID NO: 3, with a length of 386 AA and a predicted weight of 41 kDa, and about 130 copies of a FII tail tube monomer SEQ ID NO: 4 with a length of 167 AA and a predicted weight of 18 kDa. The approximate predicted molecular weight of the entire pyocin is 7700 kDa. The estimate of expression level of the R-type pyocin in induced culture was 10 mg/L. The bacteriocin produced by ATCC Accession No. PTA-124262 was effective in producing a zone of inhibition, showing bioefficacy against *D. alaskensis* in the sub-nanomolar range, i.e., on a plate at a level of 1 ppm.

Example 4: Analysis of the Effect of Whole Cell *Pseudomonas aeruginosa* EC42.15 ATCC Accession No. PTA-124262 on the Viability of *Desulfovibrio alaskensis* ATCC 14563

The viability of *D. alaskensis* ATCC 14563 was monitored in the presence of *P. aeruginosa* EC42.15 (ATCC Accession No. PTA-124262). As a control, the viability of *D. alaskensis* ATCC 14563 was also monitored in the presence of *P. aeruginosa* (ATCC Accession No. 15442), which is a *P. aeruginosa* strain that does not produce a bacteriocin that is active against *D. alaskensis*. All experiments were conducted in an anaerobic chamber, and all incubations were done at 30° C.

Stock cultures of *P. aeruginosa* ATCC Accession No. PTA-124262 and ATCC Accession No. 15442 were prepared in TSB amended with 1% (w/v) potassium nitrate (TSB-N). Stock cultures of *D. alaskensis* were prepared in ATCC® Medium 1250: Modified Baar's Medium for Sulfate Reducers with NaCl (2.5% w/v) (MB-1250). The media used for testing the effect of the *P. aeruginosa* strains on the viability of *D. alaskensis* consisted of a 1:1 mixture of the two medias noted above. *P. aeruginosa* was enumerated by observing turbidity in 96-well plates containing TSB-N. This medium also allowed for selective enumeration of *P. aeruginosa* from mixtures of this strain with *D. alaskensis*. *D. alaskensis* was enumerated by observing iron sulfide precipitation in 96-well plates containing MB-1250 with iron indicator. This medium also allowed for selective enumeration of *D. alaskensis* from mixtures of this strain with *P. aeruginosa*.

Test samples were prepared by inoculating aliquots of the 1:1 media with 1% (v/v) *P. aeruginosa* alone, 1% (v/v) *D. alaskensis* alone or 1% (v/v) each of *P. aeruginosa* and *D. alaskensis*. All test samples were enumerated for both *P. aeruginosa* and *D. alaskensis* at selected time points. The data are summarized in Table I. The dose of the whole bacteriocin-producing cells is comparable to the level of sulfate-reducing bacteria present, or ~$1\times10^6$ cfu/mL.

TABLE I

| | Single Cultures | | | Co-Cultures | | | |
| --- | --- | --- | --- | --- | --- | --- | --- |
| | *P. aeruginosa* strains alone | | *D.* | *P. aeruginosa* strains + *D. alaskensis* | | *D. alaskensis* + *P. aeruginosa* strains | |
| Time (hrs) | EC42.15 ATCC PTA-124262 | ATCC 15422 | alaskensis alone ATCC 14563 | EC42.15 ATCC PTA-124262 | ATCC 15422 | EC42.15 ATCC PTA-124262 | ATCC 15422 |
| | cfu/mL (Study #1) | | | | | | |
| 0 | 6.4E+06 | — | 6.4E+05 | 5.6E+06 | — | 5.6E+05 | — |
| 4 | 2.4E+06 | — | 2.4E+06 | 5.2E+06 | — | 5.2E+06 | — |
| 24 | 7.7E+07 | — | 5.6E+06 | 7.7E+07 | — | 5.6E+03 | — |
| 48 | 7.7E+07 | — | 5.6E+06 | 7.7E+07 | — | 5.6E+05 | — |
| | cfu/mL (Study #2) | | | | | | |
| 0 | 3.0E+05 | 4.3E+07 | 1.6E+05 | — | — | — | — |
| 4 | 3.2E+07 | 6.1E+07 | 1.4E+05 | 2.6E+07 | 6.1E+07 | 1.3E+05 | 2.4E+05 |
| 24 | 6.1E+07 | 6.1E+07 | 3.3E+06 | 6.1E+07 | 6.1E+07 | 5.2E+03 | 1.8E+04 |
| 48 | 6.1E+07 | 6.1E+07 | 1.6E+06 | 6.1E+07 | 6.1E+07 | 7.6E+02 | 4.3E+07 |
| 192 | 6.1E+07 | 3.3E+07 | 6.1E+07 | 6.1E+07 | 6.1E+07 | 1.3E+06 | 7.3E+06 |

These data demonstrate decreased viability of the *D. alaskensis* SRP strain when it is cultured in the presence of *P. aeruginosa* ATCC PTA-124262.

Each and every patent, patent application, and publication, including websites cited throughout specification are incorporated herein by reference. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

The invention claimed is:

1. A method of controlling unwanted prokaryotes in an oil or gas field environment or treatment fluid comprising:
   (a) contacting the environment or fluid with an amount of *Pseudomonas aeruginosa* bacterium, ATCC Accession No. PTA-124262 and progeny or derivatives thereof effective to produce bacteriocin virulent for the unwanted prokaryotes; or
   (b) contacting the environment or fluid with an amount of a bacteriocin produced from the bacterium of (a), wherein said bacteriocin is virulent for the unwanted prokaryotes.

2. The method according to claim 1, wherein said contacting occurs for a time sufficient to permit the bacterium to produce bacteriocin virulent for the unwanted prokaryotes or for the bacteriocin to kill the unwanted prokaryotes.

3. The method according to claim 2, wherein the unwanted prokaryotes are sulfate reducing prokaryotes (SRP).

4. The method according to claim 3, wherein the SRP is one or more of *D. alaskensis, D. desulfuricans, D. longus*, or *D. vulgaris*.

5. The method according to claim 1, further comprising contacting the environment or fluid with whole cell bacteria of, or bacteriocin or bacteriocin extract produced from, another strain of *Pseudomonas aeruginosa*, or *Thauera aminoaromatica* or *Ideonella* that can kill SRP.

* * * * *